(12) United States Patent
Lang et al.

(10) Patent No.: US 6,494,687 B2
(45) Date of Patent: Dec. 17, 2002

(54) METERING DEVICE FOR VISCOUS LIQUIDS WITH A PLURALITY OF SELECTIVELY ENGAGED METERING PUMPS, METERING CHANNELS, SUPPLY CHANNELS, AND BYPASS CHANNELS FOR FLUSH CLEANING

(75) Inventors: Andreas Lang, Marktheidenfeld (DE); Peter H. Mahler, Kreuzwertheim (DE)

(73) Assignee: Brand GmbH + CO KG, Wertheim (DE)

( * ) Notice: Subject to any disclaimer, the term of this patent is extended or adjusted under 35 U.S.C. 154(b) by 0 days.

(21) Appl. No.: 09/809,630

(22) Filed: Mar. 16, 2001

(65) Prior Publication Data

US 2001/0055533 A1 Dec. 27, 2001

(30) Foreign Application Priority Data

Mar. 20, 2000 (DE) ........................................ 100 13 528

(51) Int. Cl.[7] ............................................. F04B 49/035
(52) U.S. Cl. ..................... 417/296; 417/517; 417/518; 137/246; 222/309; 222/318; 222/321.1; 222/137; 222/265; 222/267
(58) Field of Search ................................ 417/296, 517, 417/518; 137/240; 222/309, 318, 321.1, 137, 265, 267

(56) References Cited

U.S. PATENT DOCUMENTS

| | | | |
|---|---|---|---|
| 3,168,872 A | 2/1965 | Pinkerton | 417/492 |
| 3,572,130 A | 3/1971 | Goldsmith | 73/864.12 |
| 4,008,003 A | 2/1977 | Pinkerton | 417/250 |
| 4,702,889 A | 10/1987 | Cabrera et al. | 422/103 |
| 5,305,917 A | * 4/1994 | Miller et al. | 222/137 |
| 5,718,570 A | * 2/1998 | Beckett et al. | 137/625.21 |

FOREIGN PATENT DOCUMENTS

| | | |
|---|---|---|
| DE | 1 673 224 | 9/1971 |
| DE | WO 89 10191 | * 11/1989 |
| DE | 9 013 050 | 1/1991 |
| EP | 0 399 947 | 11/1990 |
| EP | 0 363 450 | 11/1992 |
| EP | 0 545 560 | 6/1993 |
| EP | 0 454 691 | 1/1995 |
| WO | WO 89/10191 | 11/1989 |
| WO | WO 93/10432 | 5/1993 |
| WO | WO 94/01215 | 1/1994 |
| WO | WO 94/16305 | 7/1994 |

* cited by examiner

*Primary Examiner*—Charles G. Freay
*Assistant Examiner*—Emmanuel Sayoc
(74) *Attorney, Agent, or Firm*—Nixon Peabody LLP; David S. Safran (57) ABSTRACT

A metering device for liquids, especially for viscous liquids, preferably liquids which are to be metered under sterile conditions, with a plurality of metering pumps which can be simultaneously actuated. To achieve an optimized mode of operation, it is provided that the surfaces on the bottom of the pump holding plate and the top of the metering channel plate are made as adjoining sealing surfaces, forming a seal, that, in the pump holding plate, there is a bypass channel with outlet openings in the sealing surface on the bottom of the pump holding plate for each metering pump and that by the relative displacement of the pump holding plate and the metering channel plate with respect to one another, the outlet openings of the bypass channel can be moved into a position in which the bypass channel connects the respective metering channel to the respective supply channel in the metering channel plate. In this position, the respective outlet opening is also connected to the metering channel or the supply channel so that overall flushing is possible.

19 Claims, 6 Drawing Sheets

METERING DEVICE FOR VISCOUS LIQUIDS WITH A PLURALITY OF SELECTIVELY ENGAGED METERING PUMPS, METERING CHANNELS, SUPPLY CHANNELS, AND BYPASS CHANNELS FOR FLUSH CLEANING

BACKGROUND OF THE INVENTION

1. Field of the Invention

The subject matter of the invention is a metering device for liquids as is used in production shops of industry and also in the laboratory. This metering device is intended and suitable especially for viscous liquids, likewise for liquids which are difficult to meter in some other way. In particular, the metering device for liquids has one or more preferably simultaneous acting metering pumps, and is intended for liquids which are to be metered under sterile conditions.

2. Description of Related Art

The prior art discloses a metering device for liquids (U.S. Pat. No. 4,008,003). This metering device has two metering pumps which can be simultaneously actuated and which are double acting, in the form of so-called positive displacement piston pumps. Each metering pump has a double acting piston and a cylinder which holds and seals the piston with two outside connections per piston end. The connections are connected to one another and to supply and discharge lines.

With such a metering device, it is possible to meter comparatively accurately. However, it is difficult to effectively clean and flush such a metering device with metering pumps built in this manner while still keeping them in an operational state. The complexity of the overall arrangement, and especially, the guidance of a plurality of channels with many corners creates major problems. This is especially difficult when problematic, especially viscous liquids and/or liquids to be metered under sterile conditions are involved. It has been found that these metering devices do not work satisfactorily in practice.

With respect to cleaning or flushing, it is disadvantageous that a flushing liquid can only be conveyed through the system by the pumping action of the positive displacement piston pumps. The cleaning action is therefore quite limited.

SUMMARY OF THE INVENTION

Thus, it is an object of the present invention to provide a metering device for liquids, especially for problematic liquids, which is improved in its handling with respect to flushing or cleaning.

This object is achieved in accordance with the invention by a metering device for liquids with one or more preferably simultaneously acting metering pumps being provided with a pump holding plate which supports the at least one metering pump, and a metering channel plate which is parallel to the pump holding plate and has at least one metering channel for the at least one metering pump; wherein the pump holding plate has a flat bottom surface in which the at least one outlet opening of the at least one metering pump is located; wherein the metering channel plate has a top surface which sealingly adjoins the bottom surface of the pump holding plate; wherein, at the sealing surface, a respective outlet opening is adjacent to a respective supply channel; wherein the pump holding plate and the metering channel plate are movable relative to one another; wherein the at least one outlet opening of the at least one metering pump can be selectively overlapped with at least one outlet opening of at least metering channel or at least one supply channel; wherein a respective bypass channel for the at least one metering pump is located in the pump holding plate adjacent to the corresponding outlet opening; and wherein, by the relative displacement of the pump holding plate and the metering channel plate with respect to one another, the at least one outlet opening of the respective bypass channel is movable into a position in which the respective bypass channel connects the at least one respective metering channel to the at least one respective supply channel.

Such a metering device makes it possible to simultaneously meter a plurality of the same liquid volumes into a corresponding number of receiving containers with a plurality of metering pumps which are simultaneously actuated. The metering device for this purpose has a plurality of identical metering pumps which permit simultaneous intake or delivery of a host of the same volumes of liquid. It is desirable that the metering device be cleaned and flushed during operation.

The teaching of the invention can fundamentally be implemented advantageously in a metering device with only one metering pump. In particular, the teaching of the invention can be advantageously implemented with a plurality of integrated metering pumps. In a metering device with several metering pumps, the elimination of external connecting lines between the metering pumps acquires major importance in terms of construction, handling, and cleaning.

According to the invention, the channels of a metering device, which comprises at least one metering pump, are formed in the pump holding plate and the metering channel plate which can form the desired seals at all sites of interest by adjacent sealing surfaces. The distribution of channels on the pump holding plate and the metering channel plate creates the prerequisite for implementing a flow-through system for cleaning the metering device. By means of the bypass channel, specifically with outlet openings in the sealing surface on the bottom of the pump holding plate, the outlet openings of the assigned metering channel and the supply channel can optionally be connected to one another. This enables the possibility of continuous flushing of the channels of the metering device according to the invention. The prerequisite for this is that the metering channel plate, on the top, in fact, has a flat sealing surface which adjoins the bottom of the pump holding plate to form a seal. The continuous flushing of the channels is much more effective in terms of cleaning technology than flushing in the cycle of individual pump strokes, as occurs in the prior art. Moreover, it is interesting that the metering device according to the invention makes it possible to allow the metering pump to work in the flushing position, therefore to effect a flushing flow in the course of pump function.

Structurally, the metering device according to the invention is extremely feasible due to its simple channel routing without bends.

Also, an embodiment of the metering device which acquires special importance is one where, in the position where the bypass channel connects the assigned metering channel to the assigned supply channel, the assigned outlet opening is likewise connected to the metering channel or to the supply channel. In this way, backflushing of the sealing surfaces occurs. This backflushing is of major interest for a plurality of problematic applications, especially for liquids to be metered under sterile conditions.

The invention is explained below using drawings which show embodiments by way of example only.

DETAILED DESCRIPTION OF THE INVENTION

A metering device for liquids, particularly problematic liquids, for example, viscous liquids which harden when exposed to air and/or liquids which are to be metered under sterile conditions. For example, the liquid can be a single-component plastic which hardens when exposed in air, which is viscous and which must be metered under sterile conditions into receiving containers, for example, in the production of pharmaceutical and medical products.

Automatic metering of such a liquid with a metering device with a plurality of metering pumps to be simultaneously actuated imposes very high demands on the construction of the metering device. In particular, the metering device must have as few valves as possible, and, as much as possible, overall clean flat seals should be implemented. In addition, the metering device must be protected as effectively as possible against the entry of air and/or bacteria. In any case, this applies to the liquid channels in the metering device. Finally, effective flushing of the liquid channels in the metering device should and must be possible without completely disassembling the metering device.

The above explained problems also inherently apply in a metering device with only one metering pump and have been solved according to the invention for such a metering pump. Considerations relating to this invention therefore apply also to a metering device with only one metering pump even if they are explained below with respect to a preferred embodiment of a metering device with several metering pumps.

Figure 1:
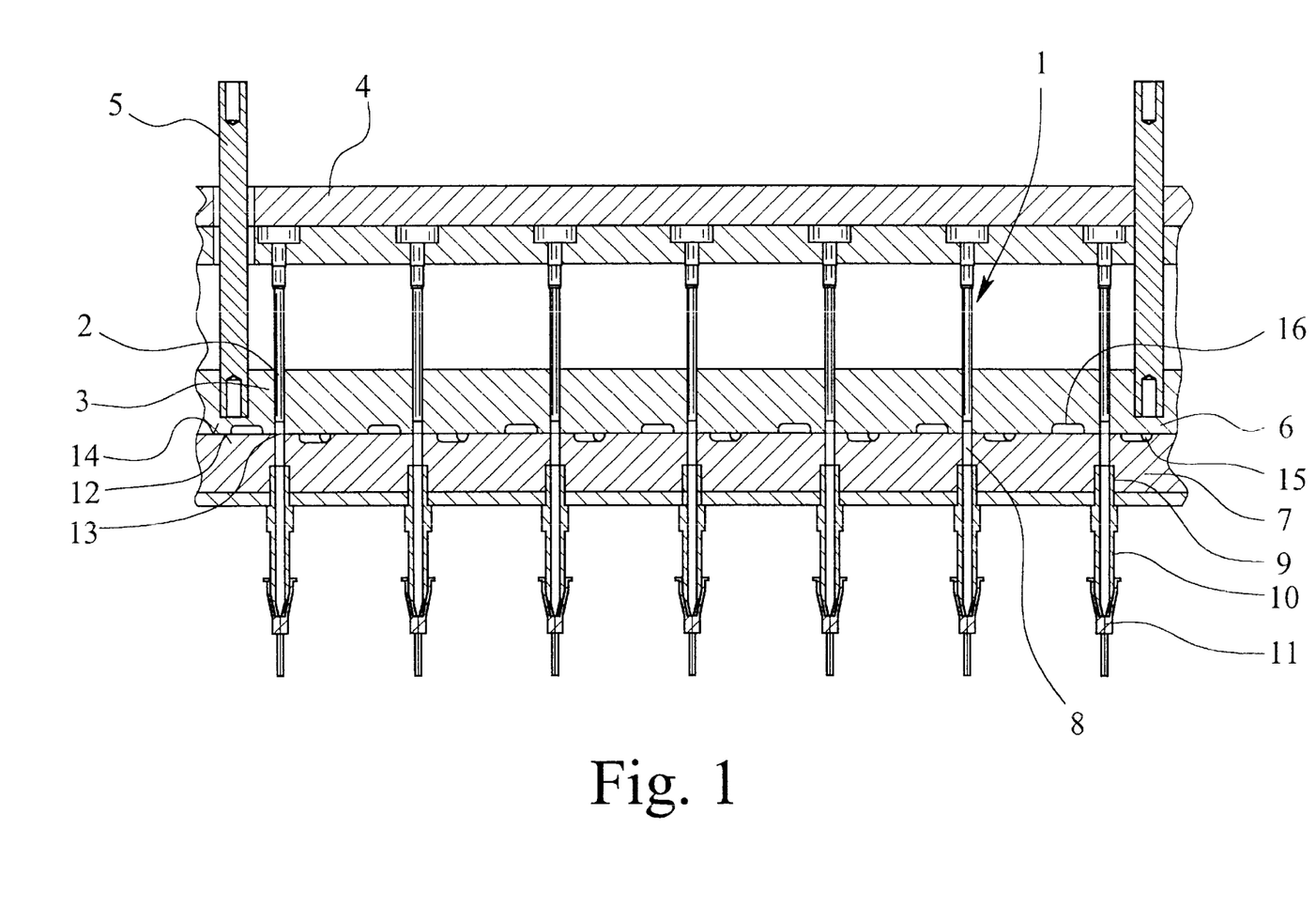
FIG. 1 is a cross-sectional view of a first embodiment of a metering device according to the invention showing linear displacement of the metering channel plate relatively to the pump holding plate.

FIG. 1 shows the metering device according to a first embodiment of the invention with a plurality of metering pumps 1 which are to be simultaneously actuated. They are executed in this embodiment as piston-cylinder arrangements with pistons 2 and cylinders 3 which have been integrated into an overall arrangement. In this embodiment, the metering device has seven metering pumps 1 in a row; the metering device can be made in one row or in several rows.

FIG. 1 shows a bridge 4 for the pistons 2 of the piston-cylinder arrangements which form the metering pumps and by which the pistons 2 of the different metering pumps I are connected to one another for synchronous motion. The bridge 4 is routed in the vertical direction on guides 5 and can be moved in the vertical direction by a motorized drive which is not further shown here.

In the metering device, there is a pump holding plate 6 by which the metering pumps 1 are supported. Furthermore, there is a metering channel plate 7 which is parallel to the pump holding plate 6 and in which there are metering channels 8 assigned to the metering pumps 1.

Each metering channel 8, in this preferred embodiment, has a receiver 9 on the bottom end in which, in the embodiment shown, a longer guide shaft 10, which projects downward, is attached thereby continuing the metering channel 8. On the bottom end of the guide shaft 10 sits a high precision outlet tip 11 which can be slipped on separately and which, in the embodiment shown, is used for precisely delivering the viscous liquid to be metered under sterile conditions into the corresponding mold receiving vessel. In the explained example, the liquid is a viscous, single-component plastic which is metered under sterile conditions into the receiving vessel.

For the reasons explained in the general part of the specification, the pump holding plate 6, on a bottom side 12 thereof, has a flat sealing surface in which outlet openings 13 of the metering pumps 1 are located. Accordingly, the metering channel plate 7, on a top side 14 thereof, has a flat sealing surface which adjoins the bottom 12 of the pump holding plate 6, forming a seal. Here, as well, we are concerned with a flat seal between the plates 6, 7, at least in the area of the outlet openings 13.

Figure 2:
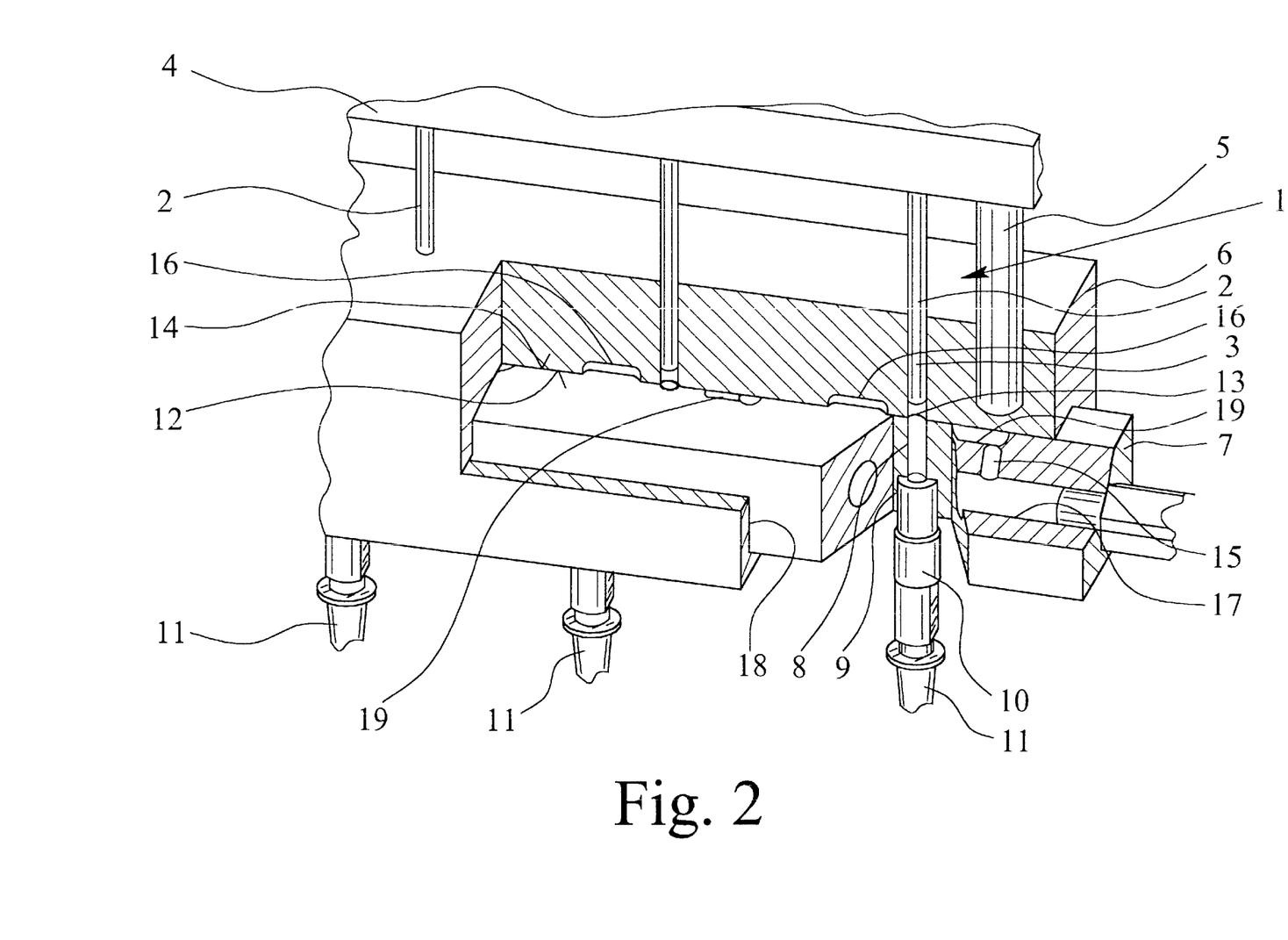
FIG. 2 shows, by way of a cut-away view, the metering device of FIG. 1 in the metering position.
Figure 3:
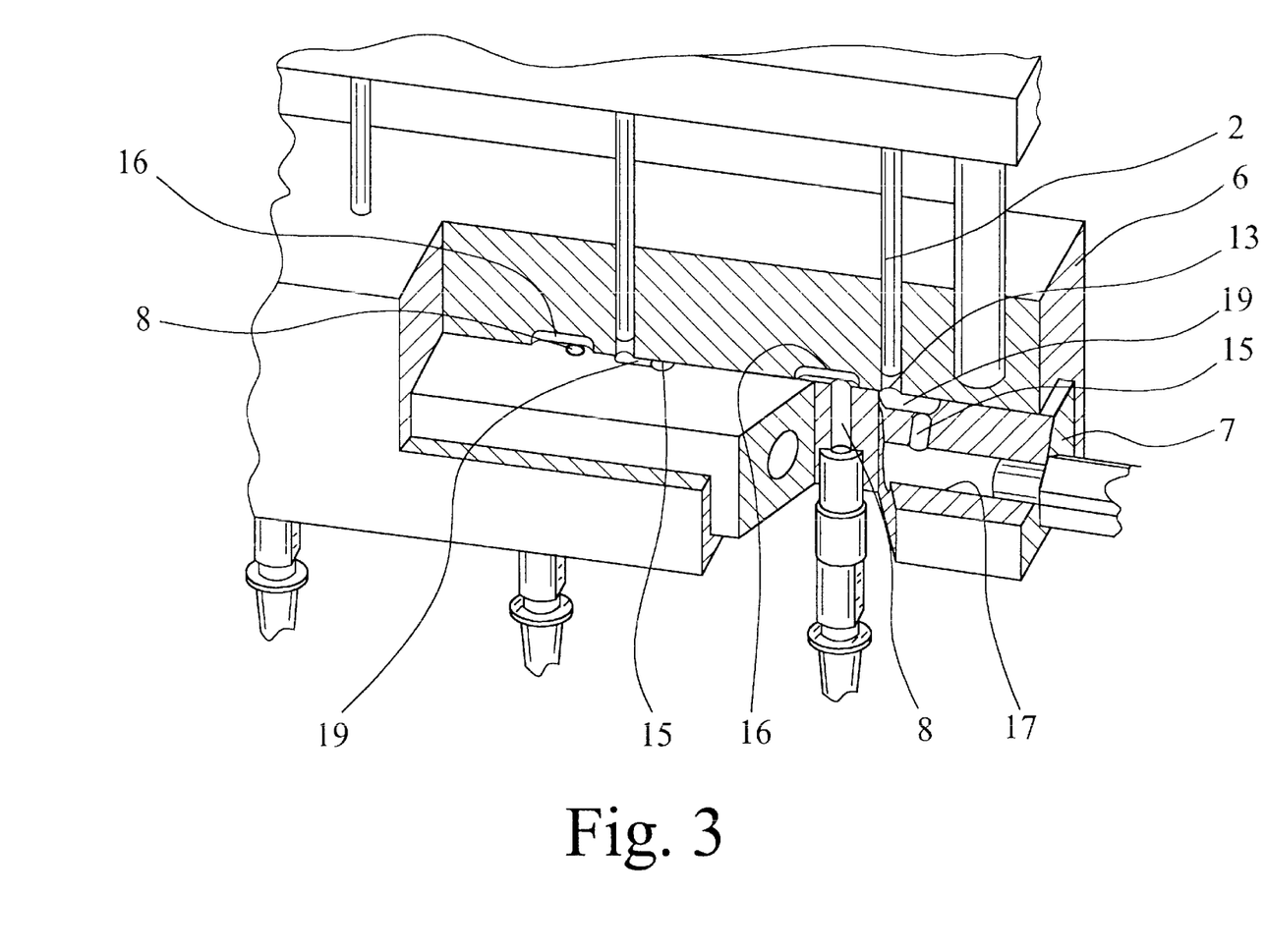
FIG. 3 shows, in a view which corresponds to FIG. 2, the metering device of FIG. 1 in the intake position.

In the sealing surface on a top side 14 of the metering channel plate 7, adjacent to one another, are the outlet openings of the metering channel 8 which are assigned to the metering pump 1 and to at least one assigned supply channel 15. FIG. 2 clearly shows this in connection with FIG. 1. In this embodiment, with displacement which takes place in the lengthwise direction, therefore from right to left or vice versa in FIG. 1, the pump holding plate 6 and the metering channel plate 7 can be moved relative to one another so that the outlet openings 13 of the metering pumps 1 can be selectively overlapped with the outlet openings of the assigned metering channels 8 or the assigned supply channels 15. Thus, there is, on the one hand, the metering position (FIGS. 1 and 2), and, on the other hand, the intake position (FIG. 3).

Furthermore, it is provided that in the pump holding plate 6 adjacent to the corresponding outlet opening 13, there is a respective bypass channel 16 which is assigned to the metering pump 1, with outlet openings in the sealing surface on the bottom 12 of the pump holding plate 6, and that by the relative displacement of the pump holding plate 6 and the metering channel plate 7 with respect to one another, the outlet openings of the bypass channel 16 can be moved into a position in which the bypass channel 16 connects the assigned metering channel 8 to the assigned supply channel 15. This concept can also be accomplished in the same way in a metering device with only one metering pump 1 which has already been addressed above.

The bypass channels 16 are shown in FIG. 1 in all positions of the seven metering pumps 1. They are arranged in the pump holding plate 6 because they can perform the task of connecting to one another, if necessary, the channels 8, 15 assigned to the respective position in the metering channel plate 7. Thus, a direct flow-through possibility of all channels 8, 15 is created in the metering channel plate 7 using the bypass channels 16 which connect them. Of course, overall, this requires a sealing action between the bottom 12 of the pump holding plate 6 and the top 14 of the metering channel plate 7; therefore, this requires sealing surfaces which adjoin one another to form a seal with a high degree of smoothness.

Figure 4:
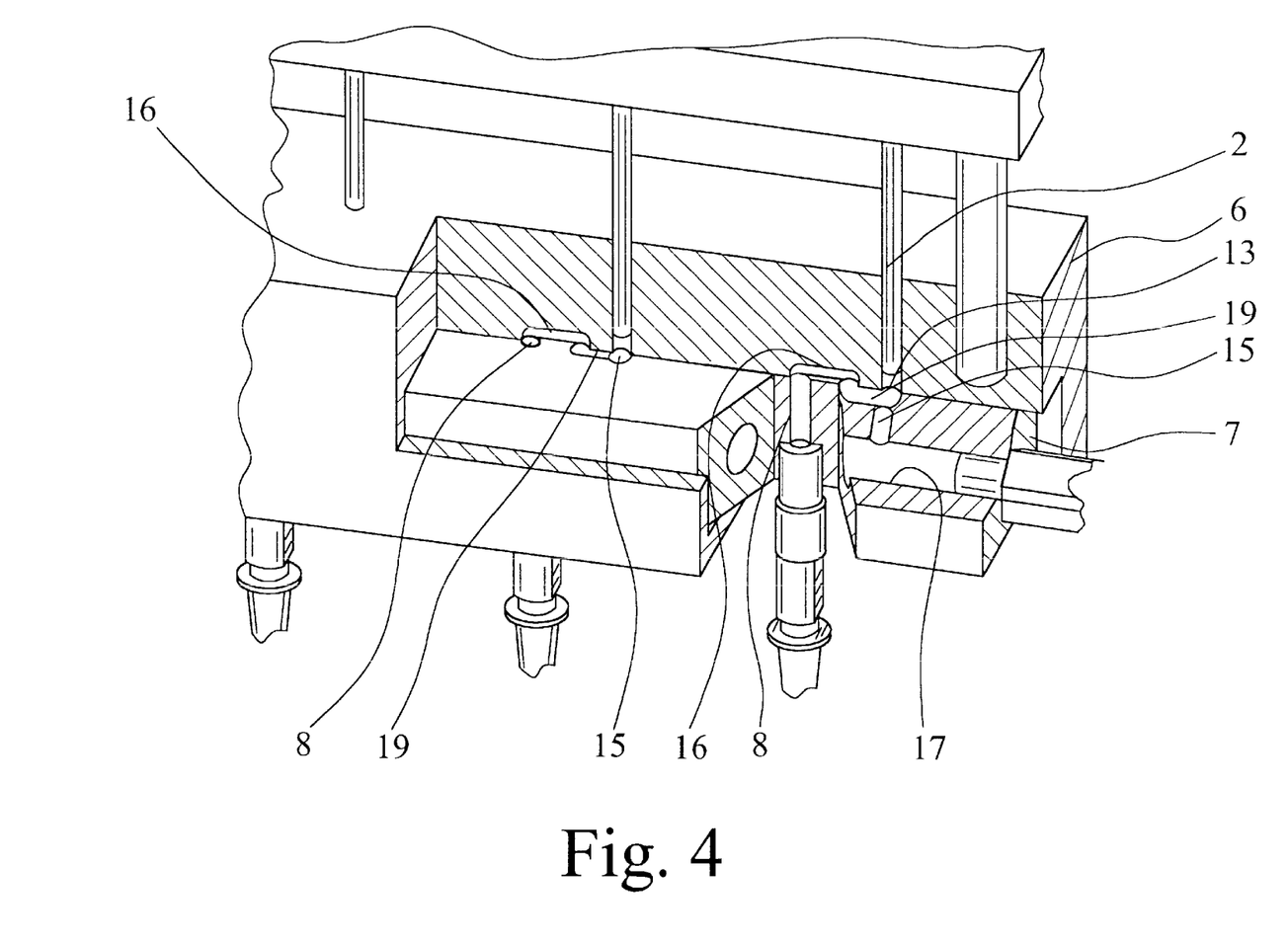
FIG. 4 shows, in a view which corresponds to FIG. 2, the metering device of FIG. 1 in the flushing position.

In the position of the metering channel plate 7, which is shown in FIG. 4, relative to the pump holding plate 6 in which the flushing function is accomplished, the flushing of the channels with continuous flow-through with a flushing medium can be accomplished; therefore, the flushing function is not dependent on implementing the quasi-static flushing with individual pump strokes which is accomplished in the prior art. With the flushing underway, the metering pumps 1 can even be allowed to run so that a flushing flow is accomplished with simultaneous pump function thereby affecting optimum flushing action.

The demands for smooth seal surfaces relate to the properties of the liquids which are to be metered with the metering device according to the invention. With very viscous liquids, which may not necessarily be sensitive to the entry of air or penetration of bacteria, an even seal is less critical compared to thin liquids or especially to liquids which are to be metered under sterile conditions. Here, in practice, the cost of production of especially flat seal surfaces will correspond with the demands.

The construction implemented according to the invention is characterized by a very simple structure of the metering device with flow guidance and with few angles, in which only a minimum number of connecting elements is necessary.

Each supply channel 15 in the metering channel plate 7 could be provided with its own connection to the outside. But, a configuration which also has structural advantages is of interest for optimally uniform feed of the metering pump 1. Specifically, it is provided according to the invention that the supply channels, or at least several of the supply channels 15, are connected to a common liquid supply line 17 in the metering channel plate 7. This also simplifies the structure, especially of the metering channel plate 7 which is already penetrated with channels anyway. The embodiment shown in FIGS. 2 to 4 shows the liquid supply line 17 in the metering channel plate 7 laterally offset to the metering channels 8 of the metering pumps 1, i.e., the channels which are located in a line. Accordingly the supply channels 15 which lead from the liquid supply line 17 to the top 14 of the metering channel plate 7 run laterally angled with respect to the supply line 17 to the outlet openings which are located on the top 14. This three-dimensional distribution of the various flow channels in the metering channel plate 7 makes it possible to accommodate all these channels without mutual collision in the metering channel plate 7 even in an arrangement of a plurality of metering pumps 1.

The drawings do not show the outer periphery of the metering device according to the invention which must encompass corresponding control means for flow control through the various channels in order to be able to implement the various functions "intake", "meter" and "flush".

With respect to the relative motion of the pump holding plate 6 and the metering channel plate 7 with respect to one another, a rotary motion can be accomplished as has been known for decades such as, especially of disk valves (published European Patent Application EP 0 399 947 A1 and EP 0 454 691 B1, and U.S. Pat. No. 4,702,889). Of course, these disk valves of the type under consideration are known in the most varied embodiments, but generally not within a metering device with a plurality of metering pumps to be simultaneously activated. Disk valves contain additional high precision parts with seal surfaces which adjoin one another to self-seal. They are often made of ceramic in order to accomplish highly smooth seals which are necessary in many areas.

The preferred embodiment of a metering device according to the invention is characterized with respect to the relative motion of the pump holding plate 6 and the metering channel plate 7 in that they can be displaced relative to one another by means of a linear motion. For this construction, with a relatively small number of metering pumps 1 to be simultaneously activated, the structure and linear motion of the preferred embodiment has major structural advantages. In particular, the metering channel plate 7 can be guided relatively easily by means of a guide receiver 18 on, or formed as part of, the pump holding plate 6. The U-shaped guide profile of the guide receiver 18, i.e., the profile which is undercut on both sides, is especially apparent in FIGS. 2 to 4.

Furthermore, FIGS. 2 to 4 show especially clearly one particular feature of the metering device according to the invention which acquires considerable importance in a structural regard. It is provided that the bypass channel 16 is made as a groove which is open towards the bottom 12 of the pump holding plate 6, and the outlet openings are formed simply by the open side of the groove. The outlet openings of the bypass channel 16 are thus essentially "formed" by the outlet openings of the metering channel 8 or of the supply channel 15 of the assigned metering pump 1.

Furthermore, FIG. 1 shows that the supply channel 15 has a section 19 which is formed as a groove which is open towards the top 14 of the metering channel plate 7, and the outlet opening of this section 19 is formed simply by the open side of this groove. Thus, a certain overlapping in the desired manner can be accomplished with a stipulated linear displacement of the metering channel plate 7 relative to the holding plate 6.

Although not shown in the drawings of the two embodiments, there can also be other channels in the metering channel plate 7. Therefore, it can be provided that, in the metering channel plate 7 of metering pump 1, there can be another channel, and the assigned bypass channel 16 or another assigned bypass channel in the pump holding plate 6 can connect the further channel in a certain relative position of the plates 6, 7 to the assigned metering channel 8 and/or the supply channel 15.

Figure 5:
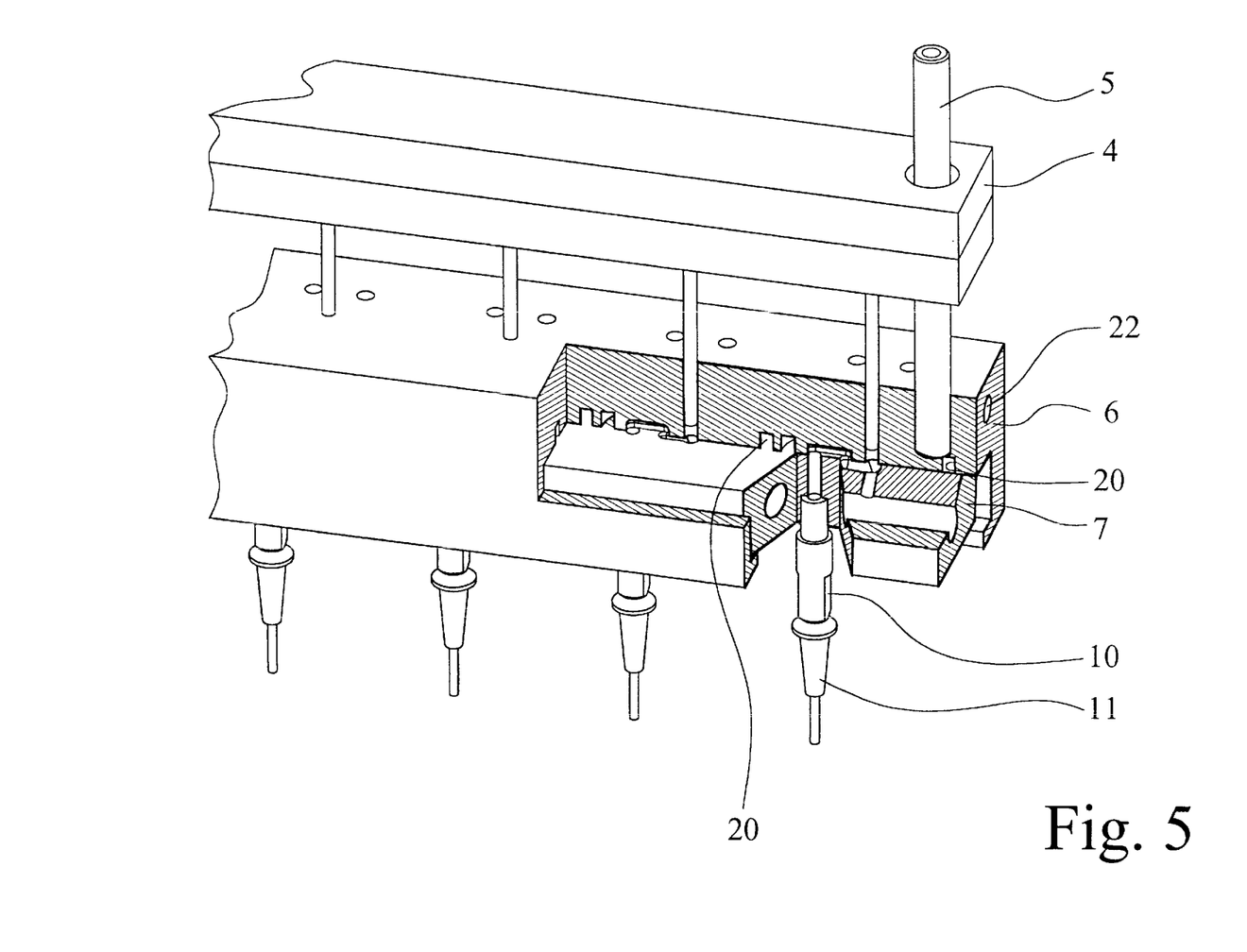
FIG. 5 shows, in a schematic, cut-away view, similar to FIG. 4, another embodiment of a metering device according to the invention in the flushing position.
Figure 6:
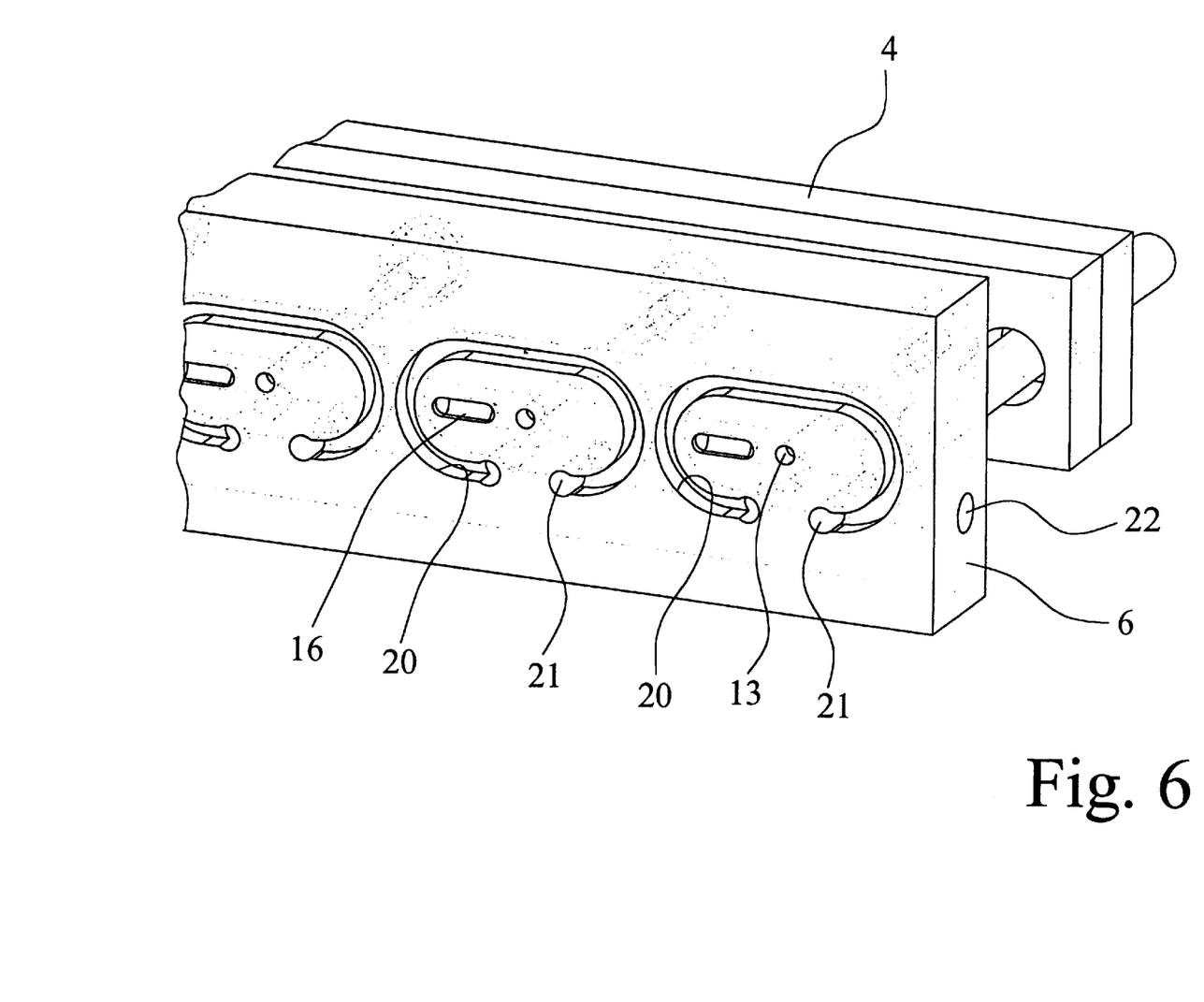
FIG. 6 is a bottom perspective view of the pump holding plate of the metering device according to the embodiment of FIG. 5.

The other embodiment of the metering device according to the invention, which is shown in FIGS. 5 & 6, does not differ in its basic structure from the first embodiment of the metering device according to the invention which is shown in FIGS. 1 to 4. Therefore, FIGS. 5 & 6 show only a few reference numbers which have already been addressed in conjunction with FIGS. 1 to 4. However, FIGS. 5 & 6, show for this embodiment of a metering device according to the invention one particular feature which will be explained below. FIG. 5 shows the flush position similar to FIG. 4.

In this embodiment, in the pump holding plate 6, on the bottom 12 of the metering pump 1, there is one flushing channel 20 which is made as a groove which is open to the bottom 12. The flushing channel 20, in any case, partially annularly surrounds all of the outlet openings assigned to each metering pump 1. Via an assigned flushing connection channel 21, flushing liquid can flow into the flushing channel 20, and on the other end, can drain again via another flushing connection channel 21. The flushing channel 20, therefore, represents a type of externally peripheral ring line with which any perhaps any leakage between the sealing surfaces in the area of the outlet openings which are assigned to this metering pump 1 can be captured by the flow of flushing liquid around it. For example, for a plastic which otherwise hardens when exposed to air, a liquid seal can be accomplished as a ring seal with the through-flowing flushing liquid; this ring seal prevents any air entry in the seal area, or if air should have entered, re-activates the water-soluble plastic by contact with, for example, water.

Flushing channels in disk valves are known (U.S. Pat. No. 4,702,889); within the framework of the teaching of the invention, these flushing channels are, however, feasibly used at a certain site, specifically relative to the respective metering pump.

FIG. 5 shows, on the top of the pump holding plate 6, blind plugs or closures which close the flushing connection channels 21 there. This corresponds to advantageous production engineering for the flushing connection channels 21. FIG. 5 shows that the flushing liquid from the supply connection 22 in the pump holding plate 6 enters the flushing channel 20 of the first metering pump 1, flows through the latter, emerges again there on the end side and enters the flushing channel 20 of the following metering pump 1 via the flushing connection channels 21 in the pump holding plate 6. Thus, the flushing liquid successively flows through the flushing channels 20 of all metering pumps 1 and ultimately leaves the pump holding plate 6 on the other end via an outlet (not shown).

Also, backflushing and flushing around the respective metering pump 1 could be provided with a corresponding flushing channel on the top of the pump holding plate 6,. This is not further shown in the drawings.

The working operation of the invention will now be explained using the first embodiment which is shown in FIGS. 1 to 4.

FIG. 2 shows the ends of the metering stroke of the metering device where the pistons 2 of the metering pumps 1 have been moved down and have metered the liquid to be metered, controlled by the metering channels 8, through the guide shafts 10 and the outlet tips 11, into receiving tanks (not shown).

FIG. 3 shows that, by lengthwise displacement of the metering channel plate 7 relative to the pump holding plate 6 (from FIG. 2) to the left, the section 19 of the supply channel 15 has been overlapped with the outlet opening 13 of the metering pump 1. If at this point the bridge 4 is moved, thereby moving the piston 2 to the top, the liquid to be metered is taken into the cylinders 3 of the metering pump 1 from the common liquid supply line 17 via the supply channels 15. This can, of course, be replaced or supported by the pressure prevailing in the liquid supply line 17.

FIG. 4 shows the position of the metering channel plate 7 relative to the pump holding plate 6 which, by further displacement of the metering channel plate 7 to the left, connects the supply channel 15 by means of the bypass channel 16 with the metering channel 8 of the respective metering pump 1. In this position, by introducing the flushing liquid via the common liquid supply line 17, the complete system can be flushed because all channels are connected to one another.

In this embodiment, the channel of the metering pump 1 to the outlet opening 13 is simultaneously encompassed because the supply channel 15 has a section which is open on the top 14 of the metering channel plate 7 which makes it possible for the supply channel 15 to simultaneously overlap both the bypass channel 16 and also the outlet opening 13 of the metering pump 1.

When flushing is performed, therefore, the metering pumps 1 can also be allowed to operate in the pump function and thus also accomplish optimum cleaning of the metering pumps 1 themselves with through-flowing flushing liquid. In other words, flushing takes place during the pump function, not only with individual strokes.

For all embodiments of this invention, it also applies that highly desirable smooth sealing surfaces can be achieved especially well when the sealing surfaces on the plates 6, 7 are formed of ceramic material with a high degree of smoothness.

What is claimed is:

1. A metering device for liquids comprising:
   at least one metering pump;
   a pump holding plate which supports the at least one metering pump;
   a metering channel plate which is parallel to the pump holding plate and has at least one metering channel and at least one supply channel for the at least one metering pump;
   wherein the pump holding plate has a flat lower surface in which at least one outlet opening of the at least one metering pump and at least one bypass channel are located;
   wherein the metering channel late has a top surface which sealingly adjoins the lower surface of the pump holding plate, and in the top surface has, positioned next to each other, the outlet opening of the metering channel and the outlet opening of the associated supply channel of the least one metering pump;
   wherein the pump holding plate and the metering channel plate are selectively movable relative to one another between a position in which the at least one outlet opening of the at least one metering pump overlaps with the outlet opening of the at least one metering channel, a position in which the at least one outlet opening of the at least one metering pump overlaps the outlet opening of the at least one supply channel, and a position in which the at least one bypass channel connects the outlet opening of the at least one metering channel to the outlet opening of the at least one supply channel.

2. The metering device of claim 1, wherein the at least one supply channel is connected to a common liquid supply line in the metering channel plate.

3. The metering device of claim 1, wherein the pump holding plate and the metering channel plate are movable relative to one another by rotary motion.

4. The metering device of claim 1, wherein the pump holding plate and the metering channel plate are movable relative to one another by linear motion.

5. The metering device of claim 1, wherein the pump holding plate has a guide receiver for sealing guidance of the metering channel plate.

6. The metering device of claim 1, wherein the at least one bypass channel comprises a groove having an open side at the lower surface of the pump holding plate.

7. The metering device of claim 6, wherein at least one of the at least one metering channel and the at least one supply channel has a section which is formed as a groove which has an open side at the top surface of the metering channel plate.

8. The metering device of claim 1, wherein at least one of the at least one metering channel and the at least one supply channel has a section which is formed as a groove which has an open side at the top surface of the metering channel plate.

9. The metering device of claim 8, wherein in the position in which the at least one bypass channel connects the at least one metering channel to the at least one supply channel, the at least one outlet opening is connected to one of the at least one metering channel and to the at least one supply channel.

10. The metering device of claim 1, wherein in the position in which the at least one bypass channel connects the at least one metering channel to the at least one supply channel, the at least one outlet opening is connected to one of the at least one metering channel and to the at least one supply channel.

11. The metering device of claim 1, wherein the at least one metering pump comprises a plurality of simultaneously actuatable metering pumps; wherein said at least one outlet opening comprises a respective outlet opening for each of the metering pumps, wherein said at least one metering channel comprises a respective metering channel for each of the metering pumps; and wherein said at least one supply channel comprises a respective supply channel for each of the metering pumps.

12. The metering device of claim 11, wherein a respective flushing channel for each of the metering pumps is provided in one of the metering channel plate and the pump holding plate, the flushing channel being an open groove which partially annularly surrounds the outlet opening of the respective metering pump; wherein a respective first flushing connection channel connects to the flushing channel for supplying flushing liquid thereto; and wherein a second flushing connection channel connects to the flushing channel for draining flushing liquid thereto.

13. The metering device of claim 1, wherein the at least one bypass the plates are made of ceramic material with a sufficient degree of smoothness to form a seal against leakage of metered fluids between the plates.

14. The metering device of claim 5, wherein the sealing surfaces of the plates are made of ceramic material with a sufficient degree of smoothness to form a seal against leakage of metered fluids between the plates.

15. The metering device of claim 6, wherein the sealing surfaces of the plates are made of ceramic material with a sufficient degree of smoothness to form a seal against leakage of metered fluids between the plates.

16. The metering device of claim 7, wherein the sealing surfaces of the plates are made of ceramic material with a sufficient degree of smoothness to form a seal against leakage of metered fluids between the plates.

17. The metering device of claim 8, wherein the sealing surfaces of the plates are made of ceramic material with a sufficient degree of smoothness to form a seal against leakage of metered fluids between the plates.

18. The metering device of claim 9, wherein the sealing surfaces of the plates are made of ceramic material with a sufficient degree of smoothness to form a seal against leakage of metered fluids between the plates.

19. The metering device of claim 10, wherein the sealing surfaces of the plates are made of ceramic material with a sufficient degree of smoothness to prevent the leakage of metered fluids between the plates.

* * * * *